(12) United States Patent
Andrae et al.

(10) Patent No.: US 7,497,856 B2
(45) Date of Patent: Mar. 3, 2009

(54) ARRANGEMENT FOR REMOTE-CONTROLLED RELEASE OF ACTIVE INGREDIENTS

(75) Inventors: Wilfried Andrae, Jena (DE); Matthias Erich Bellemann, Jena (DE); Henri Danan, Strasbourg (FR); Rainer Schmieg, Blankenhain (DE)

(73) Assignee: Fachhochschule Jena, jena (DE)

( * ) Notice: Subject to any disclaimer, the term of this patent is extended or adjusted under 35 U.S.C. 154(b) by 397 days.

(21) Appl. No.: 11/203,519

(22) Filed: Aug. 11, 2005

(65) Prior Publication Data
US 2006/0015088 A1  Jan. 19, 2006

(30) Foreign Application Priority Data
Mar. 7, 2003  (DE) ................ 103 10 825

(51) Int. Cl.
*A61K 9/22* (2006.01)
(52) U.S. Cl. ................ 604/890.1; 604/891.1
(58) Field of Classification Search .......... 604/890.1, 604/891.1, 57–64, 288.01–288.04, 285–288, 604/892.1; 335/209, 239
See application file for complete search history.

(56) References Cited

U.S. PATENT DOCUMENTS

| | | | | |
|---|---|---|---|---|
| 3,659,600 A | * | 5/1972 | Merrill ............... | 604/891.1 |
| 4,239,040 A | | 12/1980 | Hosoya et al. | |
| 4,439,197 A | * | 3/1984 | Honda et al. ............ | 604/891.1 |
| 4,507,115 A | * | 3/1985 | Kambara et al. ........... | 604/135 |
| 5,170,801 A | * | 12/1992 | Casper et al. ............... | 600/582 |
| 5,217,449 A | * | 6/1993 | Yuda et al. ............... | 604/890.1 |
| 5,279,607 A | | 1/1994 | Schentag et al. | |
| 5,562,915 A | * | 10/1996 | Lowe et al. ................ | 424/438 |
| 7,282,045 B2 | * | 10/2007 | Houzego et al. ......... | 604/890.1 |
| 2007/0248661 A1 | * | 10/2007 | Andra et al. ................ | 424/452 |

FOREIGN PATENT DOCUMENTS

| | | |
|---|---|---|
| DE | 29 28 477 | 1/1981 |
| DE | 197 45 890 | 3/1999 |
| WO | WO-01/78836 | 10/2001 |

OTHER PUBLICATIONS

Equipment and Methodology for Relating Gastrointestinal Absorption to Site of Drug Release S. P. Eriksen et al. J. Pharmaceutical Sciences 50 (1961) vol. 50, No. 2 151-156.
Evaluation of the Feasibility and Use of a Prototype Remote Drug Delivery Capsule (RDDC) for Non-Invasive Regional Drug Absorption Studies in the GI Tract of Man and Beagle Dog Alan F. Parr et al. Pharmaceutical Research, 1999 vol. 16, No. 2 266-271.
Die Bestimmung des Resorptionsortes von Eisen im Intestinalkanal mit einer ferngesteuerten Darmkapsel A. Hemmati Dtsch. Med. Wschr., 93 Nr. 31, 2 1468-1472 Aug. 1968.
Low Frequency Hyperthermia: Capacitive and Ferromagnetic Thermosed Methods Ivan A. Brezovich Department of Radiation Oncology, University of Alabama at Birmingham 82-110 1988.

* cited by examiner

*Primary Examiner*—Elvin Enad
*Assistant Examiner*—Bernard Rojas
(74) *Attorney, Agent, or Firm*—Jordan and Hamburg LLP

(57) ABSTRACT

The invention relates to an arrangement for the remote-controlled release of active ingredients which are located with a magnetic body in a cavity and which are released under the influence of heat. A substantially biocompatible device, which avoids unnecessary thermal and electromagnetic loads, is created by producing the heat required for releasing the active ingredients by rotating the body in the fluid.

14 Claims, 4 Drawing Sheets

ARRANGEMENT FOR REMOTE-CONTROLLED RELEASE OF ACTIVE INGREDIENTS

BACKGROUND OF THE INVENTION

The invention relates to an arrangement for the remote-controlled release of active ingredients according to the species of the patent claims.

In different areas of technology and biomedicine, of medical engineering in particular, there has been a continuing need for a remote-controlled release of substances out of a storage system, such as a capsule, at locations that cannot be accessed directly (e.g. within the human alimentary tract) at a desired time and without connecting this storage system via hoses, electrical lines or the like.

According to the state of the art, various means and methods are particularly known for the remote-controlled release of active ingredients within the digestive system which use capsules with a relatively complex structure. Typical examples are the so-called RF capsules [S. P. Eriksen et al., J. Pharmaceutical Sciences 50 (1961) p. 151], a small intestine capsule [A. Hemmati, Dtsch. Med. Wschr. 93 (1968) S. 1468], an HF capsule [B. Hugemann and O. Schuster, German Patent Document DE 29 28 477 (1979)], an InteliSite® capsule [A. F. Parr et al., Pharmaceutical Research 16 (1999) p. 266] and a marker for intestine diagnostic and therapeutic measures [W. Andrä und M. Wendt, DE 197 45 890 (1999)]. Other capsules are described in the U.S. Pat. Nos. 4,239,040 and 5,279,607.

All designs of the capsules known have at least one of the following disadvantages:

1. Some capsules consist of bio-incompatible components. Some include batteries, other capsules contain different metals in the form of spring bodies, heating wires or electrical conductors. Therefore, these capsules must be protected by a hermetic bio-compatible enclosure. The unintentional damage to this enclosure involves the risk that the toxically acting content comes into contact with the body tissue.
2. Other capsules have a rigid form and cannot be dissolved within the digestive system. Thus, before the capsule is swallowed, it must be ensured that the digestive system is free of stenoses on which these rigid capsules could be caught, because in such a case an operation would be necessary to remove them.
3. The principle on which the effect of some capsules is based is that in an electrically conductive part a alternating magnetic field induces eddy currents or magnetic losses that cause a temperature rise and, if a threshold temperature is reached, the opening of a seal. However, the alternating magnetic field generated outside the human body does not only have an effect in the specific partial volume of the capsule that is provided for the temperature rise but also in the electrically conductive body tissue. To avoid an excessive temperature rise by eddy currents at these locations, the product of the amplitude H and the frequency f of the magnetic field must remain under a maximum value (in the following referred to as "Brezovich Limits"), which has for example been indicated for the whole-body exposition as $4.85 \times 10^8$ A/(s×m) [I. A. Brezovich, Medical Physics Monograph 16 (1988), p. 82]. Thus, the alternating field output that can be converted into heat is limited and the reliable release function is restricted.

BRIEF SUMMARY OF THE INVENTION

The object of the invention is to design an arrangement for the remote-controlled release of active ingredients that avoids the aforementioned disadvantages.

According to the invention, this object is achieved by the elements of the first patent claim. Instead of magnetic or electrical losses in the eddy-current-exposed parts of the capsule, we use the friction losses generated by the movement of a magnetic body in a fluid. In this embodiment, the magnetic body can be directly integrated within a cavity filled with an active ingredient or it is arranged in a capsule filled with a suitable fluid and said capsule itself is positioned within the active ingredient in the cavity. Further improvements of the invention are expressed in the elements of the subclaims. The magnetic body in the form of a rotor is either rotated by a rotating magnetic field the generation of which requires at least two coils or coil pairs or by a self-triggered alternating field that requires only one coil.

BRIEF DESCRIPTION OF THE DRAWINGS

Accompanying the specification are figures which assist in illustrating the embodiments of the invention, in which.

DETAILED DESCRIPTION OF THE INVENTION

Figure 1:
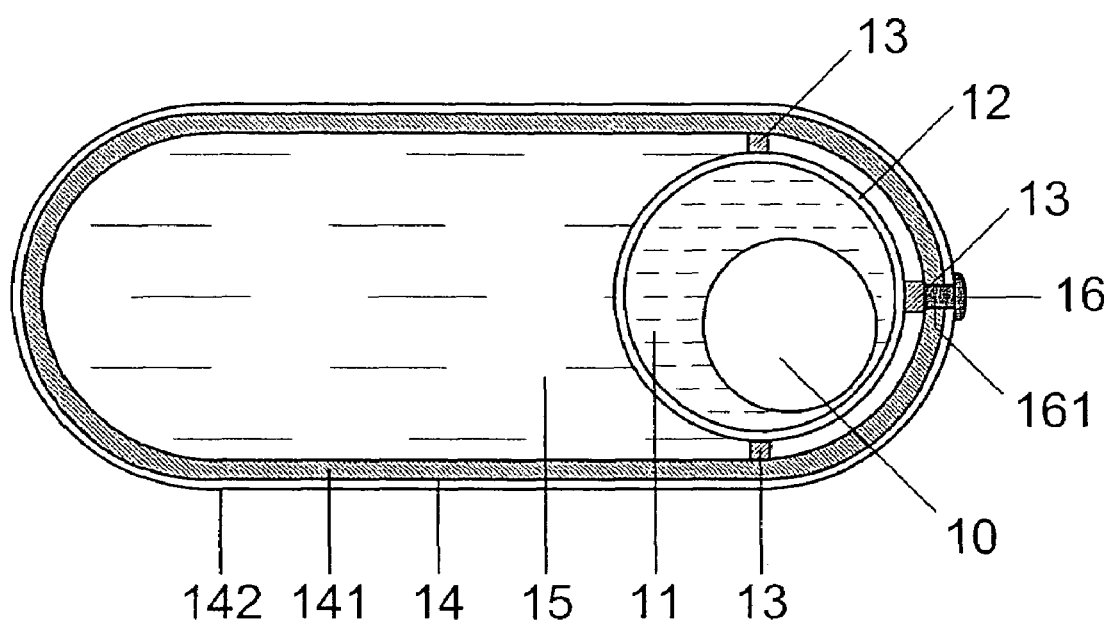
FIG. 1 is the axial section of a capsule belonging to the inventive arrangement.

In FIG. 1, spherical rotor 10 with a diameter ($\Phi$) of 5 mm is arranged in waterless fluid 11 of low viscosity in such a way that it can freely swim. Rotor 10, being a permanent-magnetic body, consists of about 50 Vol % $Fe_3O_4$ with a coercive force of $H_C$>>30 kA/m and of about 50 Vol % gelatin. It is also possible to use g-$Fe_2O_3$ instead of $Fe_3O_4$ and another atoxic, water-soluble substance (e.g. sugar) instead of gelatin. Fluid 11 is a silicone oil with a viscosity of $h=(1 \ldots 10) \times 10^{-3}$ N×s/$m^2$. Edible oil with a low viscosity can also be used instead of silicone oil. Fluid 11 is included in hollow sphere 12 which is manufactured from hard gelatin or another atoxic, water-soluble substance, e.g. sugar, and has an inner diameter of $\Phi_i$=7.6 mm and an outer diameter of $\Phi_a$=8.0 mm.

Hollow sphere 12, which can consist of two or more closely connected parts, is firmly linked to an oval or longish capsule 14 via holders 13 and is supported in said capsule that is filled with suitable active ingredient 15. The holders 13—at least one of them must be provided—consist of a mixture of about 50 Vol % gelatin and about 50 Vol % graphite; in this composition they are also suitable for the use as thermal bridges. Here, another suited substance can again replace gelatin, and instead of graphite it is possible to use silicon powder for example as an atoxic substance with a high thermal conductivity. Main, inner part 141 of capsule 14, having the standardized size 00, a diameter of $\Phi$ 8.5 mm and a length of 28 mm, consists of hard gelatin the outside of which is provided with thin coating 142, for example of polyethylene, to protect it against being dissolved by aggressive fluids, such as digestive tract fluids.

Capsule 14 is provided with opening 161 which is closed by closing element 16 consisting of paraffin wax or an animal or vegetable wax that has a melting point of between 50 and 55° C. If active ingredient 15 contains water, the interior wall of capsule 14 is also to be provided with a coating that preferably consists of the same material as the melting closing element.

Figure 2:
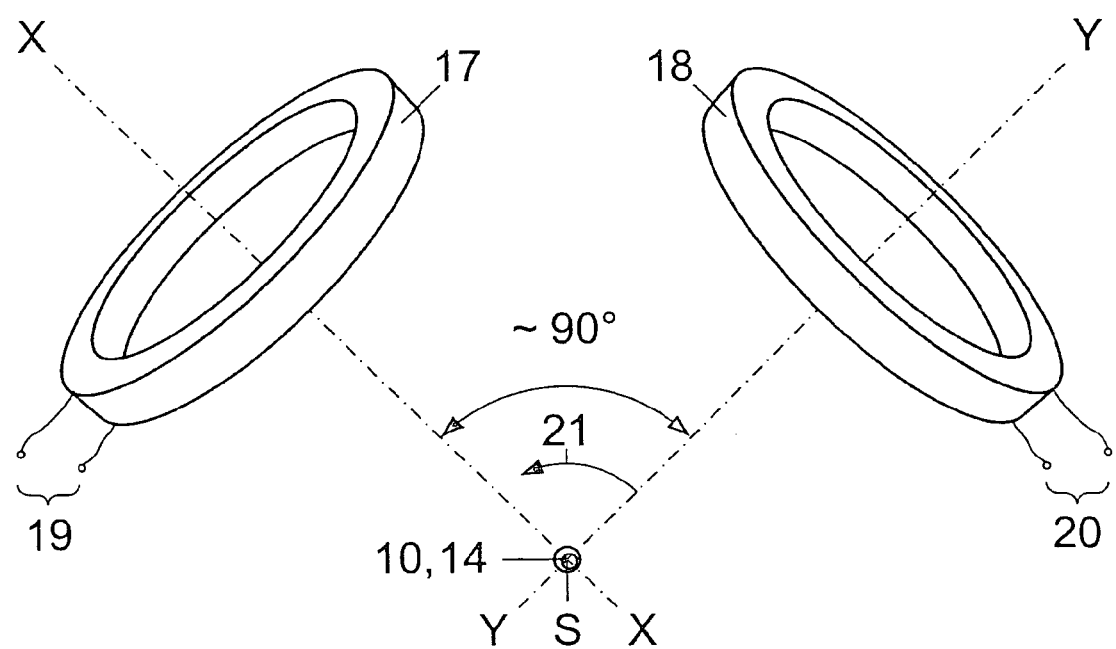
FIG. 2 is the perspective view of the coils with a capsule belonging to them in one of the inventive arrangements.

According to FIG. 2, capsule 14 described in FIG. 1 or permanent-magnetic body 10 arranged in it is located in the intersection point S or close to the intersection point of the axes X-X, Y-Y of two coils 17, 18. This point is about 15 cm away from the two coils 17, 18 that have a diameter of about 22 cm and their axes are arranged in an almost perpendicular position on top of each other. The terminals of the two coils 17, 18 are indicated by 19, 20. An alternating current flows through coils 17, 18 with a phase shift of about 90° between the two coils 17, 18 and at the location of capsule 14 it generates a rotating magnetic field that has an amplitude H of 0.3 3 kA/m at a frequency f of 1 . . . 10 kHz. 3 kA/m.

The rotating magnetic field H forces permanent-magnetic body 10 with the magnetic moment m to rotate into the direction indicated by arrow 21. For example, the magnetic field H rotates at a defined fixed speed of 1000 Hz=60,000 rotations/min. The friction between rotor 10 and fluid 11 generated during this process heats up fluid 11 and closing element 16 via hollow sphere 12 and corresponding holder 13 in such a way that it melts and active ingredient 15 can escape out of capsule 14.

To achieve maximum possible friction losses, i.e. a maximum possible temperature rise, the surface of permanent-magnetic rotor 10 is to be provided with a sufficiently high number of friction noses which can have the form of warts or wings. The amplitude of the magnetic field depends on the selected frequency and the viscosity of fluid 11 in which rotor 10 is arranged. For edible oil with a viscosity of h=0.04 N×S/m² and a selected frequency of f=500 Hz, the field amplitude must be higher than about 8 kA/m to be able to reach a temperature rise above 10 K.

The inventive arrangement overcomes the disadvantage mentioned in point 1 thanks to the fact that permanent-magnetic body 10 is manufactured from magnetit or another magnetic iron oxide that is approved as food coloring. Edible oil or another atoxic liquid can serve as the fluid. Capsule enclosures manufactured from atoxic materials are already used in medical applications.

The disadvantage mentioned in point 2 is avoided by the remote-controlled modification of the rigid form of all parts of capsule 14 into a form which can pass stenoses within the digestive tract. This is possible for permanent-magnetic body 10, because it consists of a magnetic powder that is held together by an atoxic binding agent, such as wax or gelatin which is tolerated by the intestine system. When fluid 11 is heated up by friction, not only temperature-sensitive closing element 16 of capsule 14 will be opened and active ingredient 15 will be released. Permanent-magnetic body 10 is also transferred into smaller parts (powder and deformable wax or something like that) which can pass the stenoses of the intestine.

The dissolution of the residual capsule parts is ensured by the water-soluble material (e.g. hard gelatin) they are manufactured from and which is only protected by a water-insoluble cover (e.g. of polyethylene) at such surfaces that are in contact with water or body tissue even before temperature-sensitive closing element 16 is opened. If temperature-sensitive closing element 16 has been opened and rotor 10 has disintegrated, the intestine fluid or the like can penetrate into capsule 14 and cause its dissolution from the inside.

Thanks to the inventive heat generation mechanism, the disadvantage mentioned in point 3 can be avoided, too. To explain this, the working mechanism of an inventive arrangement is compared to an arrangement according to the state of the art. In the following, heat is generated under a) by the core losses of a sphere and under b) by the friction of a permanent-magnetic sphere in a fluid of appropriate viscosity.

a) The sphere with a radius of 4 mm consists of commercially available soft-magnetic magnetit powder having an optimized packing density in terms of a maximum energy density. The magnetic poles of it are reversed in an alternating magnetic field with a frequency of 80 kHz and a selectable amplitude. In order to keep the aforementioned "Brezovich-Limit", the amplitude of the alternating field may not exceed 6 kA/m. The core losses in the sphere reach about 0.23 W. They cause a temperature rise by 7.5 K in the thermal equilibrium. But, considerable technical efforts are necessary to generate a magnetic field of 6 kA/m at a frequency of 80 kHz within the human body.

b) A sphere with a radius of 2.5 mm and a packing density of 80 Vol % magnetit is pressed from wax and a special hard-magnetic magnetit powder (coercive force: 35 kA/m). It is arranged in water within a hollow polyethylene sphere having an inner radius of 3.8 mm and an outer one of 4.0 mm. The arrangement is magnetized in a magnetic field of about 800 kA/m and then it has a remanent magnetic moment of about 0.027 A m². In clinical applications, this magnetization is performed outside the patients before they swallow the capsule. Then, a magnetic rotary field excites the internal sphere to a permanent rotation at a frequency of 6.3 kHz. During this process, the hollow sphere is held against possible rotations. For this purpose, it is integrated into a capsule in clinical applications. In the fluid, friction losses of 2.4 W are produced; that is more than the tenfold of example a) described above. The rise in temperature achieved is about 20 K in the thermal equilibrium. To overcome the viscous friction of the water, the amplitude of the rotary field must be 1.9 kA/m. Consequently, the product of the amplitude and the frequency is $1.2 \times 10^7$ A/(s×m) and thus around the factor 40 below the "Brezovich-Limit".

This shows that in example b) a considerably lower field amplitude and a lower frequency yield a thermal output that is tenfold higher than in example a). As this output distributes itself not only on the fluid volume but also on the rotor and the hollow sphere, the temperature rise really generated is only a little bit higher than double the one of example a). The product of the amplitude and frequency remains away below the "Brezovich-Limit".

However, as described above for FIG. 1, two coils or coil pairs with a phase difference of about 90° are to be operated with alternating current to generate the rotary field. But, the mentioned frequency of 6.3 kHz and the field amplitude of 1.9 kA/m can be realized with reasonable technical efforts.

Figure 3:
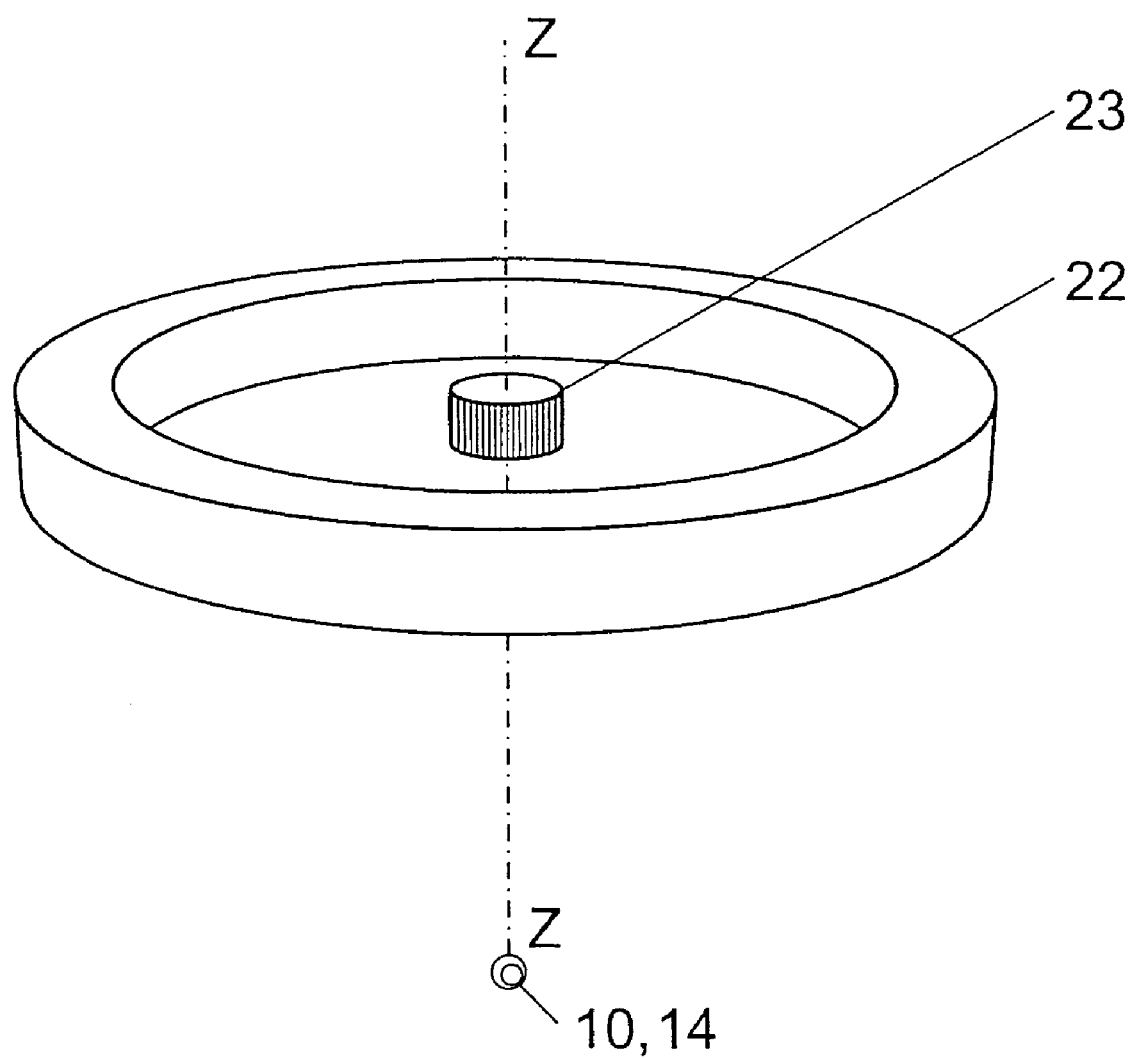
FIG. 3 is the perspective view of the inventive arrangement with only one coil.

In FIG. 3, permanent magnetic body (rotor) 10 with a magnetic moment m is arranged at a distance of about 10 cm to ring-shaped, alternating-current-carrying single coil 22 at its axis Z-Z. Coil 22 itself has a mean diameter of 15 cm. The amplitude and frequency of the alternating field H at the location of rotor 10 are identical with the ones described for FIG. 2. In the center of coil 22, sensor 23 is provided which operates for example in a magneto-resistive manner and detects the components of the magnetic rotary field. A pulse current I with a pulse-duty factor of about 1:10 flows through coil 22. That means the current passes coil 22 only during 10% of the time. During the current quiescent period the sensor is switched on.

Figure 4:
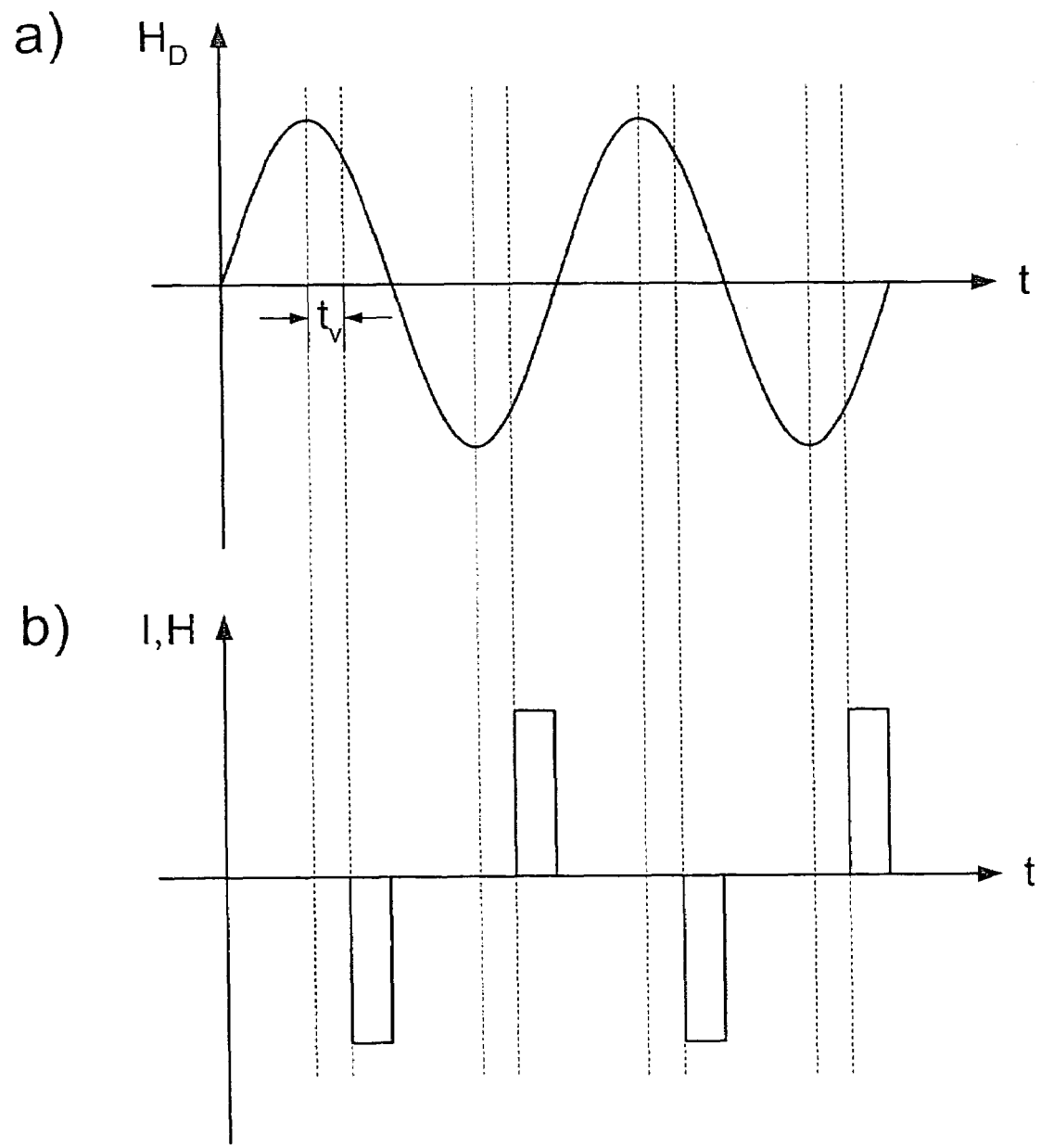
FIG. 4a is the timed succession of the z-component of the magnetic field of a rotor.
FIG. 4b is the timed succession of the current pulses and of a alternating magnetic field if only one coil is used.

The extremes of the sensor signal, which for example indicates the z component of the magnetic field $H_D$ (FIG. 4a) starting from rotor 10, are used to trigger the current pulses with an adjustable delay time t (FIG. 4b). The control of the sensor signals optimizes the delay time resulting from the comparison of the FIGS. 4a and 4b, i.e. the rotary motion of rotor 10 is maintained undamped.

The reduced number of coils caused by the self-triggered alternating field reduces the efforts as a whole. The triggering is released after the measurement of the magnetic field $H_D$ that starts from the magnetic moment m of permanent-magnetic body 10. H is the pulse-like magnetic field generated by coil 22. A time lag exists between the periodic time sequences of field H and $H_D$. It is marked by $t_v$ in FIG. 4. The pulse-like magnetic field H is turned on, when the time $t_v$ has passed after reaching the maximum value or the minimum value of field $H_D$. If this time lag $t_v$ exceeds a default value, the torque applied by the field H onto rotor 10 is sufficiently high to maintain the rotation of rotor 10. To achieve maximum possible friction losses, the shape of the rotating body can be designed in such a way that turbulences are generated in the supporting fluid. They cause higher friction losses and thus a higher rise in temperature than streams without turbulences at the same rotation frequency. This effect can be achieved by providing wart- or wing-shaped noses at a spherical body.

All elements presented in the description, the subsequent claims and the drawings can be decisive for the invention both as single elements and in any combination.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

What is claimed is:

1. An arrangement for the remote-controlled release of active ingredients which are located with a magnetic body in a cavity and are released under the influence of heat, wherein said magnetic body in said cavity is stimulated to rotate by means of an alternating magnetic field that is generated by at least one current-carrying coil from an outside and a friction of said magnetic body in a fluid produces heat which is used for releasing the active ingredient.

2. The arrangement of claim 1, wherein said magnetic body is arranged in a capsule filled with said fluid and said capsule is integrated into the cavity.

3. The arrangement of claim 1 wherein friction-increasing pieces are attached to said body.

4. The arrangement of claim 1, wherein said body consists of a permanent-magnetic material.

5. The arrangement of claim 1, wherein said alternating magnetic field is generated by at least two current-carrying coils.

6. The arrangement of claim 1, wherein said alternating magnetic field is generated by one current-carrying coil and the current of said current-carrying coil is triggered.

7. The arrangement of claim 1, wherein the currents in the coils have a phase shift of about 90° to each other.

8. Method for the remote-controlled release of active ingredients, comprising:
providing said active ingredients located with a magnetic body in a cavity, and
releasing said active ingredients by the influence of heat, wherein
said heat is produced by stimulating said magnetic body in said cavity to rotate by means of an alternating magnetic field that is generated by at least one current-carrying coil from an outside, the friction of said magnetic body in a fluid producing said heat.

9. The method of claim 8, wherein said magnetic body is arranged in a capsule filled with said fluid and said capsule is integrated into the cavity.

10. The method of claim 8, wherein friction-increasing pieces are attached to said body.

11. The method of claim 8, wherein said body consists of a permanent-magnetic material.

12. The method of claim 8, wherein said body is exposed to an alternating magnetic field that is generated by at least two current-carrying coils.

13. The method of claim 8, wherein
said alternating magnetic field is generated by one current-carrying coil, and
the current of said current-carrying coil is triggered.

14. The method of claim 8, wherein the currents in the coils have a phase shift of about 90° to each other.

* * * * *